(12) United States Patent
Mason et al.

(10) Patent No.: US 6,485,461 B1
(45) Date of Patent: Nov. 26, 2002

(54) DISPOSABLE INFUSION DEVICE

(75) Inventors: Duane R. Mason, East Dennis; John L. Brooks, III, Medfield, both of MA (US)

(73) Assignee: Insulet, Inc., Beverly, MA (US)

( * ) Notice: Subject to any disclaimer, the term of this patent is extended or adjusted under 35 U.S.C. 154(b) by 0 days.

(21) Appl. No.: 09/542,777

(22) Filed: Apr. 4, 2000

(51) Int. Cl.[7] ............................................... A61M 37/00
(52) U.S. Cl. ..................... 604/132; 604/142; 604/153
(58) Field of Search ........................... 604/132, 142, 604/153, 131

(56) References Cited

U.S. PATENT DOCUMENTS

| | | |
|---|---|---|
| 306,691 A | 3/1884 | Arai |
| 303,013 A | 8/1884 | Konopka |
| 315,727 A | 3/1885 | Arai et al. |
| 311,735 A | 10/1885 | Aran et al. |
| 405,524 A | 2/1889 | Falk et al. |
| 4,067,000 A | 1/1978 | Carlson |
| 4,108,177 A | 8/1978 | Pistor |
| 4,151,845 A | 5/1979 | Clemens |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,514,732 A | 4/1985 | Hayes, Jr. |
| 4,529,401 A | 7/1985 | Leslie et al. |
| 4,559,033 A | 12/1985 | Stephen et al. |
| 4,559,037 A | 12/1985 | Franetzki et al. |
| 4,560,979 A | 12/1985 | Rosskopk |

(List continued on next page.)

FOREIGN PATENT DOCUMENTS

| | | |
|---|---|---|
| EP | 0342947 | 5/1989 |
| EP | 0867196 | 3/1998 |
| WO | WO81/01658 | 6/1981 |
| WO | WO86/06796 | 11/1986 |
| WO | WO98/01071 | 1/1998 |
| WO | WO00/19887 | 9/1999 |
| WO | WO99/62576 | 12/1999 |
| WO | WO00/74752 | 5/2000 |
| WO | WO00/78210 | 6/2000 |
| WO | WO01/52727 | 1/2001 |

OTHER PUBLICATIONS

US 5,954,699, 12/1999, Jost et al. (withdrawn)
Web–Site Brochure. MiniMed 508. "Doing its job. Naturally." www.minimed.com/tiles/mm_113.htm.

(List continued on next page.)

Primary Examiner—Brian L. Casler
Assistant Examiner—Jeremy Thissell
(74) Attorney, Agent, or Firm—McDermott, Will & Emery

(57) ABSTRACT

A disposable device is provided which accurately and reliably delivers an infusable liquid to a patient. The infusion device includes a housing which defines a bladder chamber. A compressible bladder is disposed in the bladder chamber and is compressed by the housing upon filling the bladder with an infusable liquid to create a pressurized bladder. The infusion devices further includes a delivery system for subcutaneously delivering the infusable liquid to a body. The delivery system includes a collapsible member that supports an injection needle and a cannula. The injection needle is used to insert the cannula into the skin of the body being treated. The cannula is in communication with the bladder during delivery of the infusable liquid. The housing includes microfluidic passageways that allow communication between fluid in the bladder and the cannula.

38 Claims, 2 Drawing Sheets

U.S. PATENT DOCUMENTS

| | | |
|---|---|---|
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,755,173 A | 7/1988 | Konopka et al. |
| 4,781,693 A | 11/1988 | Martinez et al. |
| 4,801,957 A | 1/1989 | Vandemoere |
| 4,855,746 A | 8/1989 | Stacy |
| 4,882,600 A | 11/1989 | Van de Moere |
| 4,886,499 A | 12/1989 | Cirelli et al. |
| 4,898,579 A | 2/1990 | Groshong et al. |
| 4,969,874 A | 11/1990 | Michel et al. |
| 4,973,998 A | 11/1990 | Gates |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,205,819 A | 4/1993 | Ross et al. |
| 5,213,483 A | 5/1993 | Flaherty et al. |
| 5,232,439 A * | 8/1993 | Campbell et al. ............ 604/132 |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A * | 1/1994 | Weber et al. ................ 604/132 |
| 5,312,337 A | 5/1994 | Flaherty et al. |
| 5,318,540 A | 6/1994 | Athayde et al. |
| 5,342,313 A * | 8/1994 | Campbell et al. ............ 604/132 |
| 5,411,480 A | 5/1995 | Kriesel |
| 5,433,710 A | 7/1995 | VanAntwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,514,096 A * | 5/1996 | Hiejima ...................... 604/132 |
| 5,533,389 A | 7/1996 | Kamen et al. |
| 5,545,152 A | 8/1996 | Funderburk et al. |
| 5,575,770 A * | 11/1996 | Melsky et al. ............... 604/132 |
| 5,576,781 A | 11/1996 | Deleeuw |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman |
| 5,665,070 A * | 9/1997 | McPhee ...................... 604/132 |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A * | 8/1998 | Gadot ......................... 604/132 |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,875,393 A | 2/1999 | Altschul et al. |
| 5,886,647 A | 3/1999 | Badger et al. |
| 5,891,097 A * | 4/1999 | Saito et al. .................. 604/132 |
| 5,897,530 A * | 4/1999 | Jackson ...................... 604/132 |
| 5,906,597 A | 5/1999 | McPhee |
| 5,911,716 A | 6/1999 | Rake et al. |
| 5,919,167 A | 7/1999 | Mulhauser et al. |
| 5,935,099 A | 8/1999 | Peterson et al. |
| 5,954,058 A | 9/1999 | Flaherty |
| 5,957,890 A | 9/1999 | Mann et al. |
| 5,965,848 A | 10/1999 | Altschul et al. |
| 5,983,094 A | 11/1999 | Altschul et al. |
| 5,997,501 A | 12/1999 | Gross et al. |
| 6,019,747 A | 2/2000 | McPhee |
| 6,061,580 A | 5/2000 | Altschul et al. |
| 6,071,292 A | 6/2000 | Makower et al. |
| 6,144,847 A | 11/2000 | Altschul et al. |
| 6,152,898 A * | 11/2000 | Olsen ......................... 604/132 |

OTHER PUBLICATIONS

Web–Site Brochure. Applied Medical Technology. "508 Pump Information". www.applied–medical.co.uk/508.htm.

Web–Site Brochure. "The Glucose Sensor". www.animas-corp.com/sensor_f.html.

Web–Site Brochure. "the Animas R–1000 Insulin Pump". www.animascorp.com/pump_f_s.html.

Web–Site Brochure. "the Animas R–1000 Insulin Pump". www.animascorp.com/pump_f_f.html.

Web–Site Brochure. SOOIL–Homepage. "Portable Insulin Pump". www.sooil.com/intro2.htm.

Web–Site Brochure. SOOIL–Homepage. "Portable Insulin Pump". www.sooil.com/product2.htm.

Web–Site Brochure. SOOIL–Homepage. "Portable Insulin Pump". www.sooil.com/product3.htm.

* cited by examiner

DISPOSABLE INFUSION DEVICE

BACKGROUND OF THE INVENTION

Today, there are numerous medical ailments and diseases which can be treated by medicines, such as drugs, hormones, etc. One such disease is diabetes mellitus which can be characterized by the absence of or inappropriate utilization of insulin secreted by the pancreas. Insulin acts to facilitate the delivery of glucose into the cells where it undergoes various biochemical reactions. The result of diabetes is high levels of glucose in the blood and low levels of cellular glucose which can be fatal.

Generally, there are two forms of diabetes. Type I diabetes usually emerges before the age of 30 and is characterized by a reduction in the amount of insulin secreted by the pancreas. Type II diabetes is far more common and usually starts after age 30 and is characterized by normal insulin secretion but the biochemical composition of the insulin does not facilitate the glucose transport effectively.

To ameliorate this problem, conventional treatment has included one to several subcutaneous injections of insulin per day. More recently, insulin is delivered to the patient on a continuous basal basis as well as a bolus basis by a portable infusion pump, such as disclosed in U.S. Pat. No. 4,498,843 to Schneider et al These pumps typically include a syringe or cartridge filled with insulin, an electromechanical mechanism that advances the syringe or cartridge plunger, and a controller that controls the proper dosage. Catheter tubing delivers the insulin from the syringe to an infusion tubing and needle set which is inserted under the skin of the patient.

SUMMARY OF THE INVENTION

Prior art systems for delivering an infusable liquid to a body have suffered from at least two deficiencies. First, these portable systems are very expensive. For example, the initial cost alone for the system and accessories can be between 4,000 and 6,000 dollars. Recurring costs of the system and dressings can average between 200 and 300 dollars per month. Second, the catheter tubing of these systems requires a substantial amount of insulin for priming purposes which can induce inaccuracies in the delivery dosage. Further, the tubing may easily kink resulting in a loss of delivery, or insufficient dosing of, the infusable to the patient.

Accordingly, there is a need for an inexpensive and hence disposable infusion device which accurately, consistently, and reliably delivers infusable liquids, such as insulin, to a patient. In accordance with the present invention, a disposable infusion device includes a housing which defines a bladder chamber. A compressible bladder is disposed in the bladder chamber and is compressed by the housing upon filling the bladder with an infusable liquid to create a pressurized bladder. The infusion device further includes a delivery system for subcutaneously delivering the infusable liquid to the body of the user.

In accordance with one aspect of the present invention, the delivery system includes a collapsible member that supports an injection needle and a cannula. The injection needle is used to insert the cannula into the skin of the body being treated. The cannula is in communication with the bladder during delivery of the infusable liquid. In one embodiment, the housing includes microfluidic passageways that allow communication between fluid in the bladder and the cannula.

The housing includes a first side and a second side with an adhesive or adherent on the first side for attaching the infusion device to the skin of the body for a period of time, such as 3–5 days. Preferably, the adhesive forms a seal around the cannula to create a sanitary injection site into the body.

In accordance with other aspects of the present invention, the infusion device includes an alarm or radio frequency signal to warn the user when the bladder is substantially or nearly empty. This alarm can include an audible or vibrational alarm. The infusion device can also include an occlusion alarm to warn the user when a predetermined amount of infusable liquid fails to be delivered to the body.

In accordance with yet other aspects of the present invention, the infusion device includes a controller, such as a microcontroller, for controlling operation of the infusion device. For example, the controller can assess, diagnose, or transmit information about and operation of the infusion device. A power source or battery is used to power the controller. The controller is programmable, in one embodiment, for injecting predetermined amounts of infusable liquid, preferably selected by a user input, into the body.

A remote control device can be used to program and control operation of the infusion device. A signaling mechanism, such as an LED, can be included on the infusion device to confirm programming by the remote control device. The remote control device can include a memory storage device to store the programmed instructions sent to the infusion device, and to provide history information on the performance/operations of the device.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
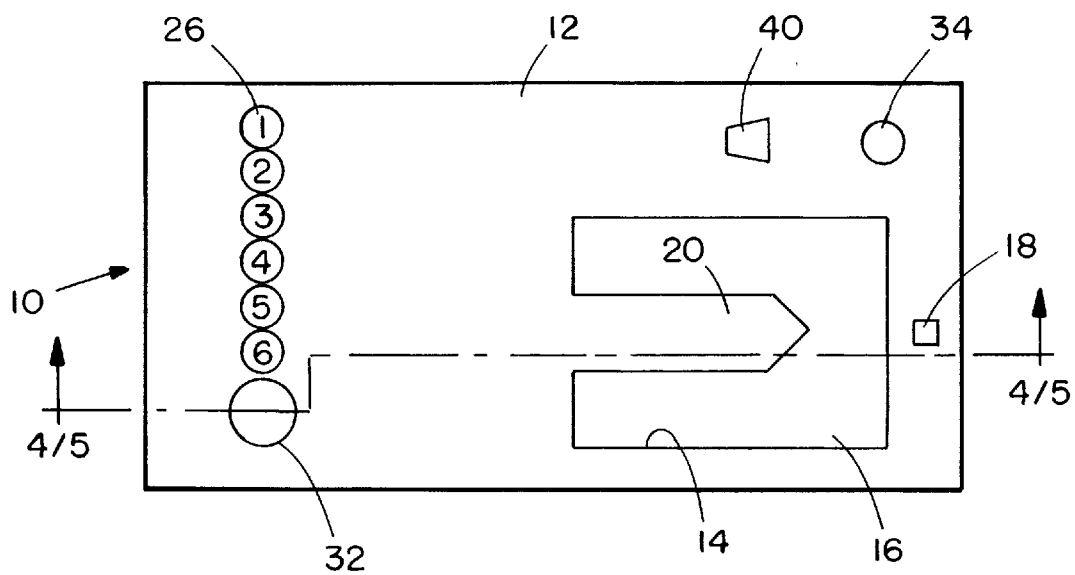
FIG. 1 is a plan view of a disposable infusion device in accordance with an embodiment of the present invention.

A description of preferred embodiments of the invention follows. FIG. 1 illustrates a limited-life, disposable infusion device or pump, generally designated as reference numeral 10. The infusion device 10 is used to deliver predetermined amounts of infusable liquid, such as liquid medicines, insulin, etc., to an injection site on the patient or user in a controlled and reliable manner. It is important that the device 10 deliver controlled amounts of infusable liquid so as to not deliver more infusable liquid than required, would could be fatal.

The infusion device 10 includes a housing 12 which is preferably constructed of a strong, heat-stable material, such as polycarbonate or a high impact styrene. The housing 12, in one embodiment, can be flexible to conform to the body to which it is attached. The housing 12 defines a bladder chamber 14 in which a bladder 16 is situated. In one embodiment, the bladder 16 is filled with insulin prior to use via an injection port 18 with a syringe. As the bladder 16 is filled, the housing 12 including a member comprising, for example, an integral cantilevered arm 20, compress the bladder to create a biasing force pressurizing the bladder for expelling the infusable therein when the pressure is relieved by actuating buttons 26 as will be described later. In alternative embodiments, arm 20 can be formed from a different material than the housing 12 and attached thereto.

The bladder 16 can formed from sheets of a durable material such as silicon, polypropylene, or vinyl sealed together to form a fluid tight compartment. In one embodiment, the bladder 16 holds up to 300 units of U-100, U-50, or U-40 insulin. Typically, the average diabetic uses about 40 units per day, not including initial priming. The infusion device 10 is capable of delivering various types of insulin, for example, ultra-fast, rapid, intermediate, and long-lasting insulin. In alternative embodiments, more than one bladder can be included in the housing 12 for delivering different types of insulin with the same infusion device 10.

Prior art devices have employed mechanisms such as stepper motors and peristaltic pumps to force the insulin from a reservoir into the user. These devices typically require heavy, powerful batteries which are carried by the user. In contrast, in one embodiment of the present invention, the housing itself provides the force for delivering the insulin to the user. This avoids heavy and costly stepper motors and the like.

Preferably, the infusion device 10 is relatively small and flexible, such as the size of a credit card. The device 10 preferably includes an adhesive 13 on the backside thereof (see FIGS. 4 and 5), such that the device can be adhered to the skin of the user for a predetermined amount of time, such as 3–5 days. Preferably, the adhesive 13 forms a seal around the injection site 15 for sanitary purposes. Thus, the device 10 can be worn at virtually all times, such as during water activities (swimming/showering) and even while sleeping.

Figure 2:
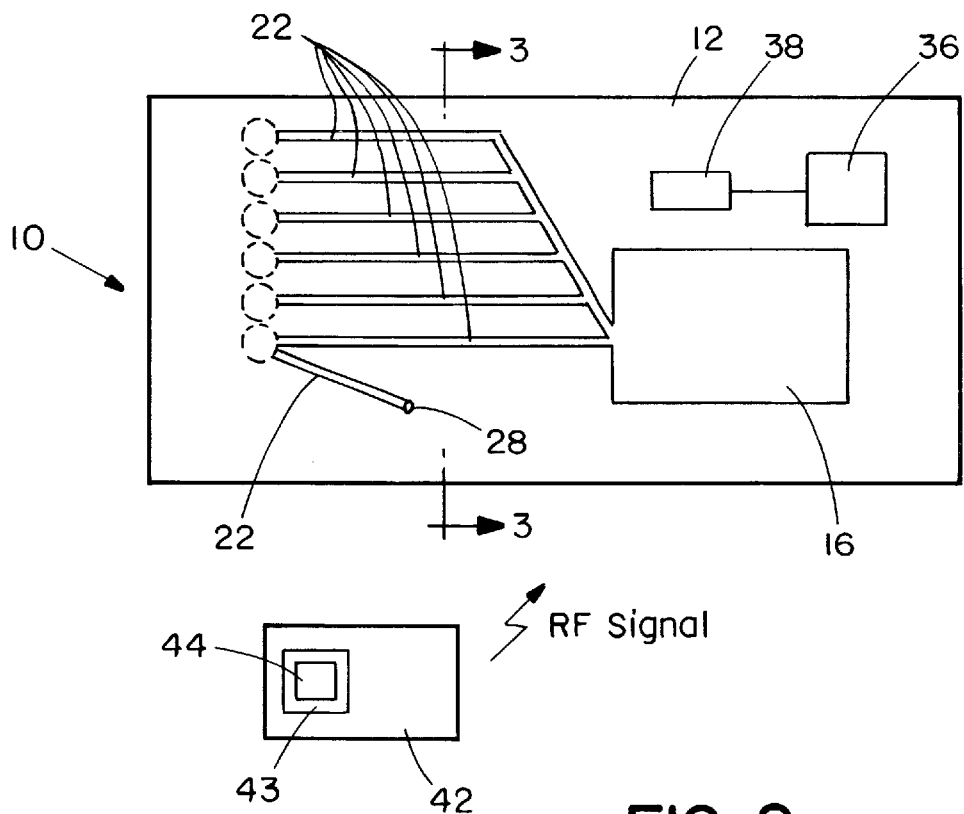
FIG. 2 is a top cut-away view of the infusion of device of FIG. 1 taken along different thickness levels to illustrate microfluidic passageways in the housing of the infusion device.
Figure 3:
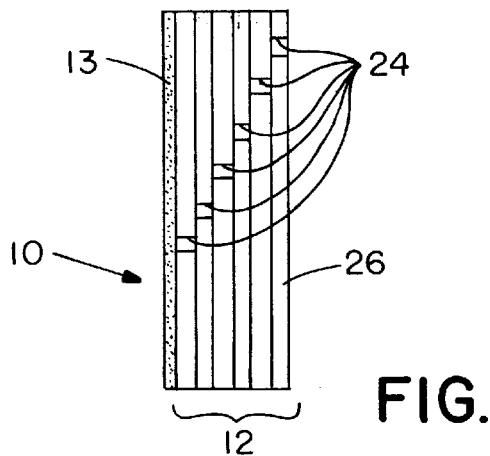
FIG. 3 is a cross-sectional view taken along line 3—3 of FIG. 2.

As illustrated in a top cut-away view of the inside of device 10 in FIG. 2, a plurality of microfluidic passageways or channels 22 provide fluid communication between the bladder 16 and the cannula 28. In one embodiment, the channels 22 vary in both length and width, as illustrated in the view of the channels in FIGS. 2 and 3. The channels 22 can be formed by laminating different layers 24 of bladder material with each layer having a channel formed therein. The channels 22 can be formed by such methods as laser etching and die-cutting. The channels 22 facilitate accurate and varying dosage levels to the user. For example, the six channels can correspond to six basal dosages. These basal rates can correspond to a range of about 0.0 to 35.0 units/ hour wherein the insulin is delivered in 0.1 unit increments. In alternative embodiments, conventional tubing, such as miniature spaghetti tubing, can be used to provide fluid communication between the bladder 16 and the cannula 28.

A plurality of buttons 26 actuate stop cocks (not shown) and function as switches which can be actuated by the user to control which of the channels 22 is selected and placed in fluid communication with the cannula 28. Alternatively, micro-electro-mechanical systems or MEMS can be used to control the channels 22 in accordance with the present invention.

The buttons/switches 26 correspond, in one embodiment, to six different basal dosages. It is understood that more basal dosages can be easily incorporated into the preferred embodiment of the invention. Furthermore, an additional button can be provided to correspond to a bolus dosage which is an additional dose of insulin. Typically, this bolus dosage is administered at or before mealtime, when glucose levels will increase with the ingestion of food. The buttons 26 can have embossed numbering thereon to aid the visually impaired. Alternatively, or in addition to, the buttons 26 can provide feedback to the operator, such as tactile or sound feedback, to confirm activation of the buttons.

As is well known in the art, the cannula 28 may be subcutaneously inserted by an injection needle or introducer needle 30. In one embodiment, the injection needle 30 is a 26 gauge needle potted in a retaining member 32. The cannula 28 is preferably made of a soft and flexible material, such as polytetrafluorethylene (PFTE). The housing 12 can be substantially transparent such that the user can visually inspect the bladder 16, the channels 22, and the injection site 15.

Figure 4:
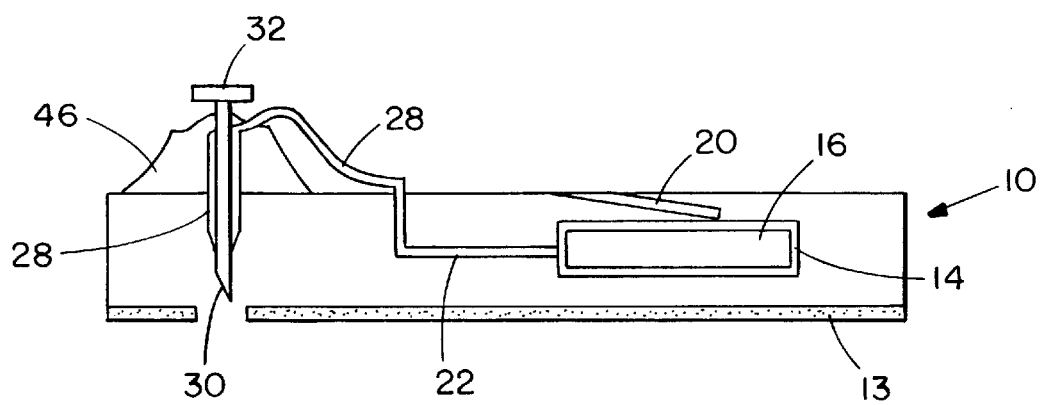
FIG. 4 is a side view of the infusion device taken along line 4/5—4/5 of FIG. 1 illustrating the injection needle and cannula in a pre-injection position prior to being inserted into the body being treated.
Figure 5:
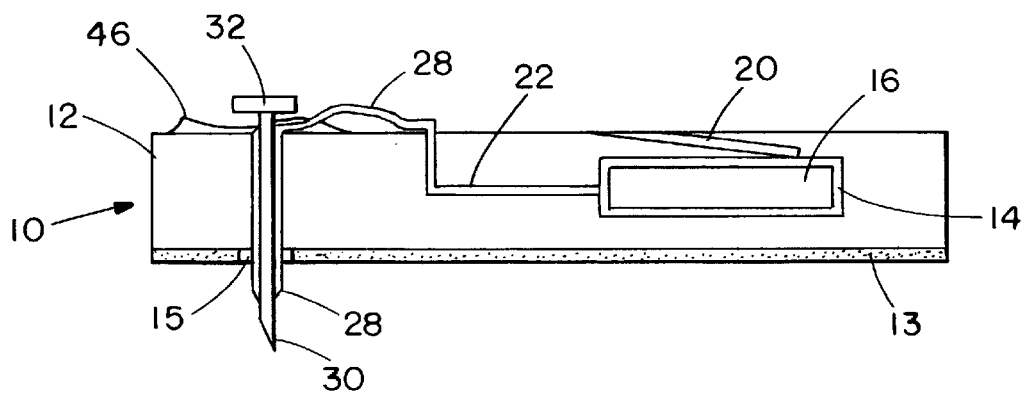
FIG. 5 is a side view of the infusion device taken along line 4/5—4/5 of FIG. 1 illustrating the injection needle in an injection position for inserting the cannula into the body being treated.

As shown in FIG. 4, the injection needle 30 and cannula 28 are supported and protected by a collapsible member 46 prior to injection. To insert the cannula 28 below the skin of the user, the retaining member 32 and needle 30 are extended toward the body being injected. FIG. 5 illustrates the introducer needle 30 in the extended position outside the housing 12 inserting the cannula 28 to a sufficient depth below the skin of the user. Because the infusion device 10 attaches directly to the skin of the user, the cannula 28 is relatively short such that kinking is avoided. Furthermore, the collapsible member 46 provides a stable base such that the cannula 28 is not easily moved around under the skin of the body. The retaining member 32 and needle 30 are withdrawn leaving the cannula 28 in place.

A firing mechanism can be used to inject the needle 30 and cannula 28 into the body. For example, a spring-loaded injector device can be used, such as disclosed in U.S. Pat. No. 5,851,197, issued on Dec. 22, 1998 to Marano et al., the contents of which are incorporated herein by reference in its entirety. In alternative embodiments, the retaining member 32 can be manually pushed into the skin by the user.

The infusion device 10 can also include an electro/ mechanical start button 34 for initiating the insulin delivery process. A controller 36, powered by a power source or battery 38, functions to control operation of the device 10. In a preferred embodiment, the controller 36 is a programmable microcontroller to control functionality of the device such as varying the basal dosage(s). Preferably, the power source is permanently attached to the housing 12.

In one embodiment, a remote control device 42 can be used to control operation of the device 10. Preferably, the device 42 includes a controller 43, such as a microcontroller, to control operation of the infusion device 10. The device 42 can employ any wireless connectivity standards, such as RF, IR, and BLUETOOTH standards, the latter being a trademark of Telefonaktiebolaget LM Ericsson, a Sweden corporation. The remote control device 42 can include functional buttons, such as a start button or bolus button to reduce accidental actuation of the same. Additionally, the device 42 can be used to program the controller 36 to vary the basal rates, for example.

The remote control device 42 in one embodiment includes a memory storage device 44 to store the programmed instructions sent to the device 10. These instructions can be later uploaded to a computer for tracking. Additionally, the memory storage device 44 can receive other information from the infusion device 10, such as how much insulin has been delivered to the body, i.e., the history of the infusion treatment. A signaling device, such as an audible or visual indicator (LED or LCD) can be incorporated onto the device 10 to confirm receipt of the instructions. Another signaling device can be incorporated onto the remote control device 42 which alerts the user when the device 42 is out of programming range, i.e., when the device 42 is too far from the infusion device 10 to program the same. This type of an alarm can be referred to as a proximity alarm. In a preferred embodiment, the remote control device 42 is small enough so as to be operable by one hand.

Preferably, the device 10 includes an alarm 40 which can be, for example, an audible alarm or a vibrational alarm. In one embodiment, the alarm 40 signals to the user when the bladder 16 is substantially or nearly empty. In another embodiment, the alarm 40 can signal when a predetermined number of insulin units (e.g., 2–4 units) are missed. This type of an alarm can be referred to as an occlusion alarm.

The housing 12 can include a unidirectional breathable material, such as Tyvek® material, disposed on the side of the housing which contacts the skin of the user. Tyvek® is a registered trademark of E.I. Du Pont de Nemours and Company. A light coating of adhesive 13 is applied over the breathable material. This allows the user's skin to breathe allowing the device 10 to remain comfortably on the user for an extended period of time. Preferably, the device 10 is waterproof such that it can be worn continuously, even in the shower.

The operation of the device will now be described. The device is provided in a sterile package and is removed therefrom for use. The bladder 16 is filled by a syringe by the user via injection port 18. The device 10 is pre-primed by the user to fill the cannula 28 with insulin. The user then removes a release liner (not shown) from the adhesive side of the infusion device 10. The device 10 is then adhered to the user, for example, at a sanitarily cleaned area of the abdomen. The cannula 28 is inserted into the skin via injection needle 30 by pressing insertion button 32. The user activates the device by pressing the start button 34 and chooses the desired dosage level by pressing a button 26. Preferably, the device 10 is discarded after a predetermined amount of time, for example, 3–4 days. Another disposable device 10 can be attached to the skin to continue the delivery process, preferably at another injection location.

While this invention has been particularly shown and described with references to preferred embodiments thereof, it will be understood by those skilled in the art that various changes in form and details may be made therein without departing from the scope of the invention encompassed by the appended claims.

What is claimed is:

1. A disposable infusion device, comprising:
   a housing defining a bladder chamber;
   a compressible bladder disposed in the bladder chamber, the bladder being compressed by the housing upon filling the bladder with an infusable liquid to create a pressurized bladder; and
   a delivery system for subcutaneously delivering the infusable liquid to a body, including a cannula and a plurality of passageways extending between the bladder and the cannula.

2. The device of claim 1, wherein the delivery system includes a collapsible member that supports an injection needle for inserting the cannula into the body.

3. The device of claim 2, wherein the housing includes an adhesive thereon for attaching the infusion device to the skin of the body.

4. The device of claim 3, wherein the adhesive forms a seal around the inserted cannula.

5. The device of claim 1, wherein the passageways that allow communication between the bladder and the cannula are microfluidic.

6. The device of claim 1, wherein the infusable liquid is insulin.

7. The device of claim 1, wherein the housing includes a member that compresses the bladder to create the pressurized bladder.

8. The device of claim 1, further comprising an alarm to warn the user when the bladder is substantially empty.

9. The device of claim 8, wherein the alarm is an audible alarm.

10. The device of claim 8, wherein the alarm is a vibrational alarm.

11. The device of claim 1, further comprising an occlusion alarm to warn the user when a predetermined amount of the infusable liquid fails to be delivered to the body.

12. The device of claim 1, further comprising a controller for controlling operation of the infusion device.

13. The device of claim 12, wherein the controller is a microcontroller.

14. The device of claim 12, wherein the controller is programmable for injecting predetermined amounts of the infusable liquid into the body.

15. The device of claim 14, further comprising a remote control device for programming the controller.

16. The device of claim 15, wherein the device includes a signaling mechanism to confirm programming by the remote control device.

17. The device of claim 15, wherein the remote control device includes a memory storage device to store the programmed instructions sent to the device and the amount of the infusable liquid delivered to the body by the infusion device.

18. The device of claim 14, wherein the predetermined amounts of the infusable liquid are selectable by a user input.

19. The device of claim 12, further comprising a power source for powering the controller, wherein the power source is permanently attached to the housing.

20. The device of claim 1, wherein each passageway includes a switch for opening the passageway and providing fluid communication through the passageway and between the cannula and the bladder.

21. The device of claim 20, wherein the switches are manually operable.

22. The device of claim 1, wherein the passageways are of varied dimensions.

23. A disposable infusion device for subcutaneously delivering an infusable liquid to a body, comprising:
    a housing defining a bladder chamber;
    a bladder disposed in the bladder chamber and being compressed by the housing for expelling the infusable liquid contained therein; and
    a cannula insertable into the skin of the body for delivering the infusable liquid to the body;
    wherein the housing includes a microfluidic passageways that independently provide fluid communication between the cannula and the bladder.

24. The device of claim 23, further comprising control means for controlling the amount of infusable liquid delivered to the body.

25. The device of claim 24, wherein the amount of the infusable liquid is selectable by a user input.

26. The device of claim 23, further comprising a controller for controlling the amount of the infusable liquid injected into the body, the controller being programmable for injecting predetermined amounts of the infusable liquid into the body.

27. The device of claim 23, wherein each passageway includes a switch for opening the passageway and providing fluid communication through the passageway and between the cannula and the bladder.

28. The device of claim 27, wherein the switches are manually operable.

29. The device of claim 23, wherein the passageways are of varied dimensions.

30. An infusion device for delivering an infusable liquid to a body, comprising:
    a housing compressing a bladder to create a pressurized bladder, the bladder being pressurized upon filling he bladder with the infusable liquid;
    an injection needle for inserting a cannula into the body, the cannula for subcutaneously delivering the infusable liquid to the body;
    microfluidic passageways in the housing that each provide fluid communication between the cannula and the bladder; and
    a control system for opening each of the passageways and controlling the amount of infusable liquid delivered to the body.

31. The device of claim 30, wherein the passageways are of varied dimensions.

32. A method for delivering an infusable liquid to a body with an infusion device, the device having a housing defining a bladder chamber and a bladder disposed therein, the bladder containing the infusable liquid therein, comprising:
    connecting the bladder to a cannula through a plurality of passageways;
    compressing the bladder to create a pressurized bladder[, the bladder being compressed by the housing upon filling the bladder with the infusable liquid];
    attaching the housing to the body; and
    inserting the cannula into the body; and
    subcutaneously delivering the infusable liquid to the body by opening at least one of the passageways.

33. The method of claim 32, further comprising compressing the bladder with the housing upon filling the bladder with the infusable liquid.

34. A method of delivering an infusable liquid to a body, comprising:
    compressing a bladder to create a pressurized bladder, the bladder being disposed within a housing of an infusion device, the housing compressing the bladder upon filling the bladder with the infusable liquid;
    inserting a cannula into the body, the cannula connected to the bladder through a plurality of passageways and subcutaneously delivering the infusable liquid to the body when in fluid communication with the pressurized bladder;
    providing fluid communication between the cannula and the bladder by opening at least one of the passageways during delivery of the infusable liquid; and
    controlling the amount of infusable liquid delivered to the body by varying dimensions of the passageways.

35. An infusion device, comprising:
    a bladder;
    a cannula for insertion into a body; and
    a plurality of passageways extending between the bladder and the cannula,
    wherein each passageway includes a switch for opening the passageway and providing fluid communication through the passageway and between the cannula and the bladder.

36. The device of claim 35, wherein the switches are manually operable.

37. The device of claim 35, wherein the passageways are of varied dimensions.

38. The device of claim 35, wherein the bladder is compressed.

* * * * *

UNITED STATES PATENT AND TRADEMARK OFFICE
CERTIFICATE OF CORRECTION

PATENT NO. : 6,485,461 B1
DATED : November 26, 2002
INVENTOR(S) : Duane R. Mason et al.

It is certified that error appears in the above-identified patent and that said Letters Patent is hereby corrected as shown below:

<u>Column 7,</u>
Line 38, after "a pressurized bladder", delete "[, the bladder being compressed by the housing upon filling the bladder with the infusable liquid]".

Signed and Sealed this

Twenty-seventh Day of May, 2003

JAMES E. ROGAN
*Director of the United States Patent and Trademark Office*